United States Patent [19]

Iwane et al.

[11] Patent Number: 5,220,079
[45] Date of Patent: Jun. 15, 1993

[54] PROCESS FOR PARA-METHYLOLATING PHENOL COMPOUNDS

[75] Inventors: Hiroshi Iwane; Takahiro Sugawara; Naoki Suzuki; Kimiko Kaneko, all of Ami, Japan

[73] Assignee: Mitsubishi Petrochemical Company Limited, Tokyo, Japan

[21] Appl. No.: 807,823

[22] PCT Filed: Jan. 11, 1991

[86] PCT No.: PCT/JP91/00017
§ 371 Date: Apr. 24, 1992
§ 102(e) Date: Apr. 24, 1992

[87] PCT Pub. No.: WO91/18858
PCT Pub. Date: Dec. 12, 1991

[30] Foreign Application Priority Data

May 25, 1990 [JP] Japan .................................. 2-135789

[51] Int. Cl.$^5$ .............................................. C07C 37/20
[52] U.S. Cl. ..................................................... 568/727
[58] Field of Search ............... 568/724, 727, 753, 764, 568/715, 716, 650

[56] References Cited

U.S. PATENT DOCUMENTS

| 4,192,959 | 4/1980 | Bauer et al. | 568/727 |
| 4,205,188 | 5/1980 | Muench et al. | 568/764 |
| 4,460,799 | 7/1984 | Perrin et al. | 568/764 |
| 5,019,656 | 5/1991 | Iwane et al. | 568/769 |

*Primary Examiner*—Werren B. Lone
*Attorney, Agent, or Firm*—Emmanuel J. Lobato; Robert E. Burns

[57] ABSTRACT

A process for preparing phenols with high selectivities, comprising reacting a phenol compound and a formaldehyde source with a quaternary ammonium as a counter cation of a phenol anion in the presence of an alcoholic organic solvent.

16 Claims, No Drawings

PROCESS FOR PARA-METHYLOLATING PHENOL COMPOUNDS

TECHNICAL FIELD

The present invention relates to a process for para-methylolating phenol compounds. More specifically, the present invention relates to a process for para-methylolating phenol compounds, comprising reacting a phenol compound with a formaldehyde source under a basic condition.

Phenol compounds of which the para-position has been hydroxymethylated are important as a variety of organic compounds such as medicines, agricultural agents and anti-oxidants or as raw materials for synthesizing them.

BACKGROUND ART

The ratio of para-/ortho-isomers in the synthesis of hydroxybenzyl alcohols comprising reacting a phenol with formaldehyde in the presence of a base catalyst is generally in the range of 1.0 or less. Thus, the main product of the reaction should be an o-hydroxybenzyl alcohol, and many reports have been presented with reference to the process for selectively preparing the o-isomer for the purpose of promoting the formation thereof.

On the other hand, since p-hydroxybenzyl alcohol is a useful compound as described above, some methods for increasing the product ratio have also been proposed. For example, there are known two methods, (1) a method for reacting phenol with paraformaldehyde in the presence of a strong basic catalyst and a polyalkylene ether (Japanese Patent Laid-Open Publication No. 141423/1980), and (2) a method for reacting phenol with paraformaldehyde in the presence of an organic nitrogen compound containing two or more nitrogen atoms in the molecule as a basic catalyst. However, as far as the present inventor knows, the content of the p-isomer in the mixture of hydroxybenzyl alcohols are 49% and 47%, respectively, in these methods, and thus the ratio of the p-/o-isomers still remains in the range no higher than 1.

Very recently, there has been reported a method for selectively synthesizing p-hydroxybenzyl alcohol with the use of cyclodextrin and substituted cyclodextrins (J. Chem. Soc., Chem. Commun., 652, 1988). This method, however, requires $\beta$-cyclodextrin, sodium hydroxide and formaldehyde in proportions of 20 to 40, of 50 and of 40, respectively, to the amount of phenol as a raw material, so that it can scarcely be said to be an industrial method in view of the cost notwithstanding its high selectivity as the ratio of the p-/o-isomers is 15.7.

Japanese Patent Laid-Open Publication No. 106833/1989 also discloses as a method for selectively hydroxymethylating the p-position of a substituted phenol a method for selectively synthesizing a phenol with the use of cyclodextrin and substituted cyclodextrin. This method also has drawbacks in that it requires catalysts such as cyclodextrin and sodium hydroxide in excessive amounts to the substituted phenol and has a low reaction velocity, so that it may be difficult to employ the method in an industrial scale in consideration of its economy.

DISCLOSURE OF THE INVENTION

An object of the present invention is to provide a process for preparing selectively an industrially useful p-hydroxybenzyl alcohols by an inexpensive method.

More specifically, the process for selectively para-methylolating a phenol according to the present invention comprises reacting a phenol compound and a formaldehyde source in the presence of an alcoholic organic solvent wherein a quaternary ammonium is used as a counter cation of the anion of the phenol compound.

A quaternary ammonium salt, particularly a tetraalkylammonium salt, is generally used as a phase transfer catalyst, and a tetraalkylammonium cation in organic synthesis is known to act as a super cation and to lead to many specific reactions. The present invention has surprisingly succeeded in enhancing extensively the selectivity of a p hydroxybenzyl alcohol with the use of the tetraalkylammonium cation.

That is, in the process according to the present invention, the ratio of p-/o-isomers is larger than 1, often 2 or more. The material to be used for increasing the ratio, i.e., the quaternary ammonium cation, is not expensive per se and used only in a small amount. Particularly when a quaternary ammonium type anion exchange resin is used as a quaternary ammonium cation, it may be reused, so that the economy of the process of the present invention is further improved.

BEST MODE FOR CARRYING OUT THE INVENTION

Phenol Compounds

Phenol compounds to be methylolated according to the present invention specifically include phenol, 2-substituted phenols, 3-substituted phenols, 3,5-disubstituted phenols, 2,5-disubstituted phenols, 2,3-disubstituted phenols, 2,3,5-trisubstituted phenols and the like. Among these compounds, phenol and 2-substituted phenols are preferred.

In this connection, the substituents are optional and include, for example, saturated or unsaturated aliphatic hydrocarbyl groups, aromatic hydrocarbyl groups, alkoxy groups, hydroxyalkyl groups, a carboxyl group, a sulfone group, an amino group, and halogens. Among these substituents, the aliphatic hydrocarbyl groups, the alkoxy groups and hydroxyalkyl groups have preferably 6 or less carbon atoms, particularly 4 or less carbon atoms.

Examples of typical substituted phenols are o-cresol, m-cresol, 2-ethylphenol, 3-ethylphenol, 2,5-dimethylphenol, 2-phenylphenol, 3-phenylphenol, guaiacol, 2-hydroxyphenethyl alcohol, 3-hydroxyphenethyl alcohol, salicylic acid, 2-chlorophenol, and 2-bromophenol.

Formaldehyde Sources

As the formaldehyde sources which are reacted with the aforementioned phenols for introducing a methylol group into the phenolic rings, formalin, paraformaldehyde, hemiformals of lower alcohols, hemiformals of polyhydric alcohols having, for example, 2 to 5 carbon atoms and the like can be mentioned, among which paraformaldehyde and the hemiformals of lower alcohols are preferred. Formalin may be used in a small amount, but the selectivity of the substitution on the phenolic ring to para-position tends to be decreased a little if the water content in the reaction system is increased. The term "formaldehyde source" in the present invention is used as a term which includes formaldehyde itself. Particularly, when formaldehyde purified from paraformaldehyde by sublimation is used, the reaction proceeds rapidly in a high yield while suppressing side-reaction.

Quaternary Ammonium Compounds

The quaternary ammonium compounds used in the present invention are the compounds which are to become quaternary ammonium cations as the counter cation of phenolates, preferably tetraalkyl ammonium cations. A group of the quaternary ammonium compounds of such a nature includes tetraalkylammonium hydroxides which form tetraalkylammonium cations as the counter cation of the phenolates, wherein the alkyl groups have 6 or less carbon atoms, preferably 4 or less carbon atoms. Specifically, the quaternary ammonium compounds include tetramethylammonium hydroxide, tetrabutylammonium hydroxide and the like. Another group of the preferred quaternary ammonium compounds includes a hydroxide form of a quaternary ammonium salt type anion exchange resin.

The phenol compound and the quaternary ammonium compound are considered to form a quaternary ammonium phenolate due to their ionic properties, and such a phenolate may be preliminarily formed prior to the methylol reaction or may be formed in situ. Thus, the aforementioned quaternary ammonium hydroxide can form a quaternary ammonium phenolate by the addition of a phenol. Furthermore, if the quaternary ammonium compound is a quaternary ammonium salt type anion exchange resin, a quaternary ammonium phenolate can be formed on the ion exchange resin by charging the Cl form of the resin into a column and anion exchanging by causing a metal phenolate such as sodium salt of a given phenol compound to flow from the top of the column.

Alcoholic Organic Solvents

The selective methylolation according to the present invention is performed in the presence of an alcoholic organic solvent.

Examples of the alcoholic organic solvents suitable for use in the process of the present invention are (i) alkanols having carbon atoms in a range of the order of 1 to 10 such as methanol, ethanol, n-propanol, i-propanol, n-butanol and i-butanol; (ii) polyhydric alcohols having carbon atoms in a range of the order of 2 to 10 such as ethylene glycol and 2,3-butanediol; and (iii) alcohols having an aromatic ring such as benzyl alcohol and the like, which are used alone or in admixture thereof within and/or between the groups. Among these solvents, lower alcohols preferably having 1 to 4 carbon atoms such as ethanol, n-propanol, i-propanol, i-butanol are preferred because these alcohols provide the para-methylolation reaction with increased selectivity and velocity of the reaction.

The para-methylolation according to the present invention is conducted in the presence of an alcoholic organic solvent, which means that a non-alcoholic organic solvent can be used in admixture with the alcohols. As the non-alcoholic solvent which can be mixed, a variety of organic solvents, for example (i) aromatic hydrocarbons such as benzene, toluene, and xylene, (ii) aliphatic hydrocarbons such as pentane, hexane, and heptane, (iii) halogenated alkyls such as chloroform, dichloromethane, and dichloroethane, (iv) amides such as dimethylacetamide and dimethylformamide, (v) sulfoxides such as dimethylsulfoxide, (vi) nitriles such as acetonitrile and benzonitrile can be mentioned.

While the percentage ratio of the non-alcoholic solvent to be mixed is not particularly limited as long as the alcoholic organic solvent has a substantial effectiveness, it is preferably in the range no higher than 70% by weight. If the non-alcoholic solvent is used in an amount greater than 70% by weight, the reaction velocity will tend to decrease. It is generally preferable to use a solvent comprising solely of an alcohol (alone or as a mixture of alcohols).

Reaction Condition

Provided that the para-methylolation is performed selectively with the use of the aforedescribed raw materials for the reactions, the reaction conditions and the reaction operations can be any suitable ones.

Specifically, for example, if a tetraalkylammonium hydroxide is used as the quaternary ammonium compound, the reaction is conducted so that the phenol compound in a proportion of 0.1 to 10 moles, preferably 0.5 to 3 moles to 1 liter of the aforementioned solvent, the tetraalkylammonium hydroxide is added in a proportion of 0.01 to 10 equivalents, preferably 0.1 to 1.2 equivalents to the phenol compound and the formaldehyde compound is added in a proportion of 0.01 to 10 equivalents, preferably 0.1 to 3 equivalents to the phenol compound.

Also, when the quaternary ammonium phenolate in which the Cl form of the quaternary ammonium salt type anion exchange resin has been anion-exchanged with a sodium phenolate of a given phenol compound is used, the solvent is used in at least an amount to ensure that the resin particles will be completely immersed in the solvent, and the reaction is conducted by adding thereto the formaldehyde source in a proportion of 0.01 to 10 equivalents, preferably 0.1 to 3 equivalents to the quaternary ammonium phenolate. The reaction temperature is in the range of 0° to 130° C., preferably 20° to 70° C.

The reaction time depends on the reaction temperatures and the kind of solvents, being ordinarily in the range of 24 to 72 hours at a reaction temperature of 50° C. While the selectivity to the p-isomer is increased somewhat in the reaction at a lower temperature, the reaction rate is lowered as well.

The reaction is generally conducted by stirring with heating under a nitrogen atmosphere or heating in a sealed tube.

The methylol derivative, particularly the p-methylol derivative may be recovered from the reaction products by a conventional method.

EXAMPLES

The present invention is further described in detail below with reference to examples. In this connection, the analysis and determination of the reaction products were carried out by HPLC (high precision liquid chromatography).

EXAMPLE 1

A commercially available 10% solution of tetramethylammonium hydroxide in methanol (manufactured by TOKYO KASEI CO.) was subjected to solvent exchange with isopropanol to produce a solution of tetramethylammonium hydroxide in isopropanol. To a 3.83 ml portion of the solution (2.24 mmoles of tetramethylammonium hydroxide) was added 0.211 g of phenol (2.24 mmoles) to produce a solution of tetramethylammonium phenolate in isopropanol.

To the solution was added 2.48 ml of a paraformaldehyde-isopropanol solution (1.12 mmoles as formaldehyde). The reaction system was purged with nitrogen, and stirring was conducted with heating at 50° C. for 115 hours to complete the reaction.

The yield was 37.6% based on the formaldehyde.

The product was a mixture consisting of 81.6% of p-hydroxybenzyl alcohol, 12.1% of o-hydroxybenzyl alcohol and 6.3% of dimethylol phenol.

At an initial stage of the reaction in which no dimethylol phenol has yet been formed, p-hydroxybenzyl alcohol is in, a proportion of 87.1% and the ratio of p-/o-products is 6.75 at this stage.

EXAMPLE 2

To 5.53 ml of a commercially available 10% tetra-n-butylammonium hydroxide-isopropanol solution (manufactured by TOKYO KASEI CO.; 1.69 mmoles of tetra-n-butylammonium hydroxide) were added 1.87 ml of a paraformaldehyde-isopropanol solution (0.85 mmole as formaldehyde) and 0.157 g of phenol (1.69 mmoles). The reaction system was purged with nitrogen, and stirring was conducted with heating at 50° C. for 20 hours to complete the reaction.

The yield was 30.3% based on the formaldehyde.

The product was a mixture consisting of p-hydroxybenzyl alcohol, o-hydroxybenzyl alcohol and dimethylol phenol, and the proportion of the p-hydroxybenzyl alcohol was 75.9%.

At an initial stage of the reaction in which no dimethylol phenol has yet been formed, p-hydroxybenzyl alcohol is in a proportion of 82.7% and the ratio of p-/o-isomers is 4.79 at this stage.

COMPARATIVE EXAMPLE 1

The reaction was conducted in the system in Example 1 except that the counter cation of phenol was sodium.

Phenol (0.211 g, 2.24 mmoles) and sodium hydroxide (0.094 g, 2.24 mmoles) were added to 3.83 ml of isopropanol, and the mixture was stirred with heating at 70° C. under a nitrogen atmosphere to form a solution. The reaction solution was cooled to room temperature, and 2.48 ml of paraformaldehyde-isopropanol solution (1.12 mmoles of formaldehyde) was added to the reaction solution. The system was purged with nitrogen, and stirring was conducted with heating at 50° C. for 24 hours to complete the reaction.

The yield was 38.1% based on the formaldehyde.

The product was a mixture consisting of three compounds, p-hydroxybenzyl alcohol, o-hydroxybenzyl alcohol and dimethylol phenol, and the proportion of the p-hydroxybenzyl alcohol was 34.1%.

At an initial stage of the reaction in which no dimethylol phenol has yet been formed, p hydroxybenzyl alcohol is in a proportion of 38.5% and the ratio of p-/o-products is 0.63 at this stage.

EXAMPLE 3

A commercially available quaternary ammonium salt type anion exchange resin ("DIAION SA10A" manufactured by Mitsubishi Chemical Industries, Ltd., strong base resin, gel form) was charged into a column and washed with water. Then 0.5 mole/lit. of an aqueous sodium phenolate solution was caused to flow through the column to substitute a chloride ion with a phenolate ion. After the resin was washed with water within the column, it was poured into a Buchner funnel, washed with water while filtration was carried out under suction to completely remove the excessive amount of sodium phenolate, and further washed with isopropanol to remove water adhering to the resin.

To 10 ml of the phenolate form quaternary ammonium anion exchange resin thus prepared was added 3.5 ml of a paraformaldehyde-isopropanol solution (2.35 mmoles of formaldehyde), and the mixture was heated at 50° C. under a nitrogen atmosphere for 30 hours to complete the reaction.

The temperature was lowered to room temperature. The resin was poured into a column, and phenol derivatives were eluted with an aqueous 1N-HCl solution from the ion exchange resin. The product was a mixture consisting of p-hydroxybenzyl alcohol, o-hydroxybenzyl alcohol and dimethylol phenol, and the proportion of the p-hydroxybenzyl alcohol to the total amount of the three compounds was 65.3%. At an initial stage of the reaction in which no dimethylol phenol has yet been formed, p-hydroxybenzyl alcohol is in a proportion of 74.1% and the ratio of p-/o-isomers is 2.86 at this stage.

EXAMPLE 4

To 5.20 ml of a commercially available 10% tetramethylammonium hydroxide-methanol solution (manufactured by TOKYO KASEI; 5.05 mmole equivalents) was added 0.6264 g of guaiacol (5.05 mmoles), and methanol was removed under reduced pressure. To the residue was added 10 ml of isopropanol, and the alcohol was removed under reduced pressure again. Finally 5 ml of isopropanol was added to obtain about 7 ml of a tetramethylammonium-2-methoxyphenolate-isopropanol solution (containing 5.05 mmoles of guaiacol).

OPERATION 1

To the solution was added 3.78 ml of a solution in isopropanol of formaldehyde purified by sublimation (2.53 mmoles as formaldehyde), and the mixture was purged with nitrogen and stirred with heating at 40° C. for 48 hours to complete the reaction.

The yield was 81.2% based on the formaldehyde.

The product was a mixture consisting of 4-hydroxymethyl-2-methoxyphenol, 6-hydroxymethyl-2-methoxyphenol and 4,6-dihydroxymethyl-2-methoxyphenol, and the proportions of the three products were 80.2%, 10.3% and 9.5%, respectively. At an initial stage of the reaction in which no dimethylol derivative had yet been formed, the proportion of the 4-hydroxymethyl-2-methoxyphenol relative to the product was 89.1%, and the selectivity to the p-position of the reaction can thus be said to be 89.1%.

COMPARATIVE EXAMPLE 2

In a 15-ml volume sealed pressure glass reactor were placed 5.0 ml of isopropanol, 0.614 g of guaiacol (4.92 mmoles) and 0.209 g of sodium hydroxide (4.92 mmoles). After the reactor was purged with nitrogen, the mixture was stirred with heating at 80° C. to form a solution. After the temperature was lowered to room temperature, 3.67 ml of a solution in isopropanol of formaldehyde purified by sublimation (2.46 mmoles as formaldehyde) was added, and the mixture was purged with nitrogen and stirred with heating at 50° C. for 14 hours to complete the reaction.

The yield was 97.6% based on the formaldehyde.

The product was a mixture consisting of 4-hydroxymethyl-2-methoxyphenol, 6-hydroxymethyl-2-methoxyphenol and 4,6-dihydroxymethyl-2-methoxyphenol, and the proportions of the three products were 11.5%, 73.6% and 14.9%, respectively. At an initial stage of the reaction in which no dimethylol derivative had yet been formed, the percentage ratio of the 4-hydroxymethyl-2-methoxyphenol to the product was 14.2%, and the selectivity to the p-position of the reaction can thus be said to be 14.2%.

EXAMPLE 5

To 5.28 ml of a commercially available 10% tetramethylammonium hydroxide-methanol solution (manufactured by TOKYO KASEI; 5.13 mmole equivalents) was added 0.555 g of o-cresol (5.13 mmoles). About 7 ml of a tetramethylammonium-2-methoxyphenolate-isopropanol solution (containing 5.13 mmoles of o-cresol) was obtained in the same manner as in Operation 1 in Example 4.

To the solution was added 3.84 ml of a solution in isopropanol of formaldehyde purified by sublimation (2.57 mmoles as formaldehyde), and the mixture was purged with nitrogen and stirred with heating at 40° C. for 64 hours to complete the reaction.

The yield was 87.9% based on the formaldehyde.

The product was a mixture consisting of 4-hydroxymethyl-2-methylphenol, 6-hydroxymethyl-2-methylphenol and 4,6-dihydroxymethyl-2-methylphenol, and the proportions of the three products were 85.1%, 8.1% and 6.8%, respectively. At an initial stage of the reaction in which no dimethylol derivative had yet been formed, the proportion of the 4 hydroxymethyl-2-methylphenol relative to the product was 91.4%, and the selectivity to the p-position of the reaction can thus be said to be 91.4%.

COMPARATIVE EXAMPLE 3

In a 15-ml volume sealed pressure glass reactor were placed 5.0 ml of isopropanol, 0.555 g of o-cresol (5.13 mmoles) and 0.216 g of sodium hydroxide (5.13 mmoles). After the reactor was purged with nitrogen, the content mixture was stirred with heating at 80° C. to form a solution. After the temperature was lowered to room temperature, 3.82 ml of a solution in isopropanol of formaldehyde purified by sublimation (2.56 mmoles as formaldehyde) was added, and the mixture was purged with nitrogen and stirred with heating at 50° C. for 43 hours to complete the reaction.

The yield was 86.0% based on the formaldehyde.

The product was a mixture consisting of 4-hydroxymethyl-2-methylphenol, 6-hydroxymethyl 2-methylphenol and 4,6-dihydroxymethyl-2-methylphenol, and the proportions of the three products were 25.6%, 53.8% and 20.6%, respectively. At an initial stage of the reaction in which no dimethylol derivative had yet been formed, the proportion of the 4-hydroxymethyl 2-methylphenol relative to the product was 36.2%, and the selectivity to the p-position of the reaction can thus be said to be 36.2%.

EXAMPLE 6

To 5.40 ml of a commercially available 10% tetramethylammonium hydroxide-methanol solution (manufactured by TOKYO KASEI; 5.24 mmole equivalents) was added 0.566 g of m-cresol (5.24 mmoles), and about 7 ml of a tetramethylammonium-3-methylphenolate isopropanol solution (containing 5.24 mmoles of m-cresol) was obtained in the same manner as in Operation 1 in Example 4.

To the solution was added 3.91 ml of a solution in isopropanol of formaldehyde purified by sublimation (2.62 mmoles as formaldehyde), and the mixture was purged with nitrogen and stirred with heating at 40° C. for 120 hours to complete the reaction.

The yield was 90.4% based on the formaldehyde.

The product was a mixture consisting of 4-hydroxymethyl-3-methylphenol, 6-hydroxymethyl-3-methylphenol and 2-hydroxymethyl-3-methylphenol and dimethylol derivatives such as 4,6-dihydroxymethyl-3-methylphenol and the like. The proportions of the 4-hydroxymethyl-3-methylphenol relative to the product was 70.4%. At an initial stage of the reaction in which no dimethylol derivative had yet been formed, the proportion of the 4-hydroxymethyl-3-methylphenol relative to the products was 79.6%, and the selectivity to the p-position of the reaction can thus be said to be 79.6%.

COMPARATIVE EXAMPLE 4

To a 15-ml volume sealed pressure glass reactor were placed 5.0 ml of isopropanol, 0.521 g of m-cresol (4.81 mmoles) and 0.205 g of sodium hydroxide (4.81 mmoles). After the reactor was purged with nitrogen, the mixture was stirred with heating at 80° C. to form a solution. After the temperature was lowered to room temperature, 3.58 ml of a solution in isopropanol of formaldehyde purified by sublimation (2.40 mmoles as formaldehyde) was added, and the mixture was purged with nitrogen and stirred with heating at 50° C. for 19 hours to complete the reaction.

The yield was 84.3% based on formaldehyde.

The product was a mixture consisting of 4-hydroxymethyl-3-methylphenol, 6-hydroxymethyl-3-methylphenol, 2-hydroxymethyl-3-methylphenol and dimethylol derivatives such as 4,6-dihydroxymethyl-3-methylphenol and the like. The proportion of the 4-hydroxymethyl-3-methylphenol relative to the product was 7.3%. At an initial stage of the reaction in which no dimethylol derivative had yet been formed, the ratio of 4-hydroxymethyl-3-methylphenol to the product was 12.3%, and the selectivity to the p-position of the reaction can thus be said to be 12.3%.

APPLICABILITY IN INDUSTRY

According to the present invention, p-methylolated derivatives of phenol compounds can be prepared inexpensively and easily. The p-methylolated derivatives are useful as medicines, agricultural agents and antioxidants, or as raw materials for synthesizing them. Thus, the present invention can be applied advantageously to the production of these organic compounds.

What is claimed is:

1. A process for selectively para-methylolating a phenol which comprises reacting a phenol compound and a formaldehyde source in the presence of an alcoholic organic solvent selected from the group consisting of an alkanol having 1 to 10 carbon atoms and a polyhydric alcohol having 2 to 10 carbon atoms at a temperature of about 0° to 130° C., wherein a quaternary ammonium cation is used as a counter cation of the anion of the phenol compound during the reaction in an amount of 0.01 to 10 equivalents based on the phenol compound used and the reaction is continued until substantially complete to thereby produce p-methylolated product in a p-isomer/o-isomer ration greater than 1.

2. A process according to claim 1, wherein the phenol compound is phenol.

3. A process according to claim 1, wherein the phenol compound is a substituted phenol.

4. A process according to claim 3, wherein the substituted phenol is a 2-substituted phenol, a 3-substituted phenol, a 3,5-disubstituted phenol, a 2,5-disubstituted phenol, a 2,3-disubstituted phenol or a 2,3,5-trisubstituted phenol.

5. A process according to claim 4, wherein the substituted phenol is a 2-substituted phenol.

6. A process according to claim 3, wherein the substituent of the substituted phenol is an aliphatic hydrocarbyl group, an alkoxy group or a hydroxyalkyl group having 6 or less carbon atoms.

7. A process according to any one of claims 1 to 6, wherein the formaldehyde source is formaldehyde, formalin, paraformaldehyde, hemiformals of lower alcohols, or hemiformals of polyhydric alcohols having 2 to 5 carbon atoms.

8. A process according to claim 1 or 2, wherein the quaternary ammonium cation originates from a quaternary ammonium compound which is a tetraalkylammonium hydroxide or a hydroxide form of an anion-exchange resin of quaternary ammonium salt type.

9. A process according to claim 8, wherein the tetraalkylammonium hydroxide is a tetramethylammonium hydroxide or tetrabutylammonium hydroxide.

10. A process according to any one of claims 1 to 6, wherein the alcoholic organic solvent is a lower alcohol.

11. A process according to claim 10, wherein the lower alcohol is ethanol, n-propanol, i-propanol or i-butanol, alone or in admixture thereof.

12. A process according to any one of claims 1 to 6, wherein the reaction is carried out by adding the phenol compound in a proportion of 0.1 to 10 moles to 1 liter of the alcoholic organic solvent and the formaldehyde source in a proportion of 0.01 to 10 equivalents to the phenol compound.

13. A process according to any one of claims 1 to 6, wherein anion exchange resin particles having thereon a quaternary ammonium phenolate comprising the quaternary ammonium salt type anion exchange resin as the quaternary ammonium compound and a given phenol compound and the formaldehyde source compound in a proportion of 0.001 to 10 equivalents of the phenolate are reacted in the presence of the alcoholic organic solvent in an amount to ensure that the particles are completely immersed in the solvent.

14. A process according to claim 8, wherein the quaternary ammonium compound is a tetraalkylammonium hydroxide having up to 6 carbon atoms in each alkyl group.

15. A process according to claim 8, wherein the quaternary ammonium compound is the hydroxide form of an anion-exchange resin of quaternary ammonium salt type.

16. A process according to claim 1, wherein the amount of said quaternary ammonium compound is 0.1 to 10 equivalents based on the phenol compound used.

* * * * *